United States Patent [19]

Perrone et al.

[11] Patent Number: 5,416,208
[45] Date of Patent: May 16, 1995

[54] PROCESS FOR PENEMS

[75] Inventors: Ettore Perrone, Boffalora Ticino; Marco Alpegiani, Milan; Franco Zarini, Settimo Milanese; Giuseppe Mazzini; Giovanni Franceschi, both of Milan, all of Italy

[73] Assignee: Farmitalia Carlo Erba S r l, Milan, Italy

[21] Appl. No.: 199,963

[22] Filed: Feb. 22, 1994

Related U.S. Application Data

[63] Continuation of Ser. No. 77,967, Jun. 18, 1993, abandoned, which is a continuation of Ser. No. 655,458, Mar. 5, 1991, abandoned.

[30] Foreign Application Priority Data

Jul. 5, 1989 [GB] United Kingdom ............... 8915392

[51] Int. Cl.⁶ .................... A61K 31/425; C07D 499/00
[52] U.S. Cl. .................................. 540/310; 514/192; 514/195
[58] Field of Search ............... 540/310, 312; 514/192, 514/195

[56] References Cited

U.S. PATENT DOCUMENTS 4,952,577  8/1990  Alpegiani et al. ............... 540/310

FOREIGN PATENT DOCUMENTS 0199446  10/1986  European Pat. Off. .
0295100  12/1988  European Pat. Off. .
2512027   3/1983  France .
2207133   1/1989  United Kingdom .

OTHER PUBLICATIONS

Chemical Abstracts, vol. 102, No. 25, 24 Jun. 1985, (Columbus, Ohio, US) see p. 593, abstract No. 220862x & JP, A, 59212488 (Kyoto Pharmaceutical Industries, Ltd.) 1 Dec. 1984.

Marco Alpegiani et al, "On the Preparation of 4-Hydroxymethyl-5-Methyl-1,3-Dioxol-2-One," Synthetic Communications, 22(9), pp. 1277-1282 (May 1992).

Marco Alpegiani et al, "Synthesis and Biological Properties of FCE 25199, A New Oral Penem," The Journal of Antibiotics, vol. 45, No. 5, pp. 797-801, (May 1992).

Primary Examiner—Nicholas Rizzo
Attorney, Agent, or Firm—Oblon, Spivak, McClelland, Maier, & Neustadt

[57] ABSTRACT

Antibacterial penems of formula (I), where R represents a hydrogen atom or a hydroxy protecting group, are prepared by reacting a β-lactam of formula (II) with an oxalyl halide in an inert solvent in the presence of an organic or inorganic base or an acid scavenger to produce a compound of formula (III), wherein X is a halogen atom, treating the resultant compound of formula (III) with a 1,3-dioxolen-2-one of formula (IV), wherein Y is a hydroxy group, in the presence of molecular sieves or an organic or inorganic base to produce a compound of formula (V), and cyclizing the compound of formula (V) in the presence of a trialkylphosphite to provide the penems of formula (I).

19 Claims, No Drawings

PROCESS FOR PENEMS

This application is a Continuation of application Ser. No. 08/077,967, filed Jun. 18, 1993, abandoned, which is a Continuation of application Ser. No. 07/655,458, filed Mar. 5, 1991, abandoned, which was filed as International Application No. PCT/EP90/01060 on Jul. 3, 1990.

The present invention relates to a process for preparing 2-methoxymethyl penem useful as antibacterial agent and to the preparation of the intermediates useful in the synthesis.

More particularly the invention relates to a process for the preparation of compounds of formula (I):

I wherein R represents a hydrogen atom or a hydroxy protecting group, which process comprises reacting a compound of formula (II)

II wherein R is as defined above, with an oxalyl halide in an inert solvent; optionally converting the resultant compound of the formula III

III wherein R is as defined above and X is a halogen atom into a compound of the formula III in which X represents a hydroxy group by hydrolysis; and either (i) treating the compound of formula III in which X is a halogen atom with a compound of the formula IV

IV wherein Y is a hydroxy group in the presence of an acid scavenger or an organic or inorganic base or (ii) treating the compound of the formula III in which X is a hydroxy group, with a compound of the formula IV in which Y is a leaving group in the presence of a base; and finally cyclizing the resultant compound of the formula V

V wherein R is as defined above and optionally deprotecting the resultant compound of the formula I wherein R is a hydroxy protecting group to obtain a compound of the formula I wherein R is a hydrogen atom.

The hydroxy protecting group which R may represent include:
  a) a silyl group —$SiR^1R^2R^3$ wherein $R^1$, $R^2$, $R^3$ are each independently $C_1$-$C_6$ alkyl, aryl, $C_1$-$C_6$ alkoxy, aryloxy or halogen atom;
  b) a $$-\underset{R^4}{\overset{}{\mathrm{CH}}}-\mathrm{A}-R^5$$

group wherein $R^4$ is hydrogen, $C_1$-$C_6$ alkyl or aryl, A is oxygen or sulphur atom, $R^5$ is an optionally substituted $C_1$-$C_6$ alkyl, aryl or heterocyclyl group or $R^4$ and $R^5$ taken together form a part of a $C_5$-$C_6$ ring
  c) a $$-\underset{\overset{\|}{\mathrm{O}}}{\mathrm{C}}R^6$$

group wherein $R^6$ is an optionally substituted alkyl, alkenyl, aryl, heterocyclyl or heterocyclylmethyl group
  d) a $$-\underset{\overset{\|}{\mathrm{O}}}{\mathrm{C}}-\mathrm{W}-R^7$$

wherein $R^7$ is hydrogen or as defined above under $R^6$ and W is a bond, a carbonyl $$(-\underset{\overset{\|}{\mathrm{O}}}{\mathrm{C}}-),\ -\underset{\overset{\|}{\mathrm{O}}}{\mathrm{C}}-\mathrm{O}-$$

or a $$-\mathrm{N}\underset{R^7}{\overset{R^4}{\diagup}}$$

group wherein $R^4$ and $R^7$ are as defined above.
Preferred hydroxy protecting R groups are a) trimethylsilyl, triethylsilyl, tert.butyldimethylsilyl, thexyldimethylsilyl, tert.butoxydiphenylsilyl b) methoxymethyl, methylthiomethyl, benzyloxymethyl, tert.butoxymethyl, tetrahydropyranyl, tetrahyrothiopyranyl, tetrahydrofuranyl, 4-methoxytetrahydropyranyl, 1-ethoxyethyl, 1-phenoxyethyl c) allyloxycarbonyl, benzyloxycarbonyl, trimethyl silylethoxycarbonyl, p-nitrobenzyloxycarbonyl, p-methoxybenzyloxycarbonyl, o-nitrobenzyloxycarbonyl, 3,4-dimethoxybenzyloxycarbonyl, phenoxycarbonyl, vinyloxycarbonyl, trichloroethoxycarbonyl, d) formyl, acetyl, propionyl, butyryl, $C_5-C_{14}$ alkanoyl, benzoyl, phenylacetyl, phenoxyacetyl, chloroacetyl, dichloroacetyl, trichloroacetyl, trifluoroacetyl, methoxyacetyl, pivaloyl, crotonyl, acrylyl, glyoxylyl, methoxyoxalyl, allyloxyoxalyl, (5-methyl-2-oxo-1,3-dioxolen-4-yl)methoxyoxalyl, butoxyoxalyl, phenoxyoxalyl, oxamyl, carbamoyl.

Preferred leaving groups which Y may represent in the formula IV include halogen atom, $C_1-C_4$ alkylsulphonyloxy and arylsulphonyloxy groups.

In the present specification, halogen atom include bromine, chorine and iodine.

A $C_1-C_6$ alkyl may be methyl, ethyl, i-propyl, propyl, n-butyl, sec-butyl or ter-butyl groups.

Alkenyl may be an allyl, propenyl or butenyl group.

Aryl is a benzene ring optionally substituted by one or more methyl, nitro, methoxy, methoxycarbonyl, cyano, hydroxy, acetamido, carbamoyl.

Heterocyclyl group is 5-methyl-2-oxo-1,3-dioxolen-4-yl, furyl, thiophenyl, benzothiophenyl, thiazolyl, triazolyl, tetrazolyl, pyridyl, pyrimidyl.

The compounds of formula I and their use as antibacterial agents are described in the published European Patent Application No. 295,100.

The present invention also provides a process for preparing a compound of formula (IV) in which Y is hydroxy group, which process comprises treating a compound of the formula IV, wherein Y is a halogen atom with silver nitrate and reducing the resultant compound by dissolving metal reduction.

The process of the present invention provides penems of formula (I) in good yield and high optical purity.

It differs from the prior art in that the synthesis consists of fewer steps, even realizable in one single pot, with appreciably improved yields and industrial feasibility.

On the contrary, in the above cited EP 295,100 conversion of azetidinones II to penems I was carried out through a multistep sequence generally requiring temporary protection of the carboxylate moiety and/or proceeding in low overall yield.

The starting material of formula (II) can be conveniently prepared as described in the above cited EP-A-295,100. The present invention therefore allows the synthesis of compounds of formula (I) as summarized in the following Reaction Scheme.

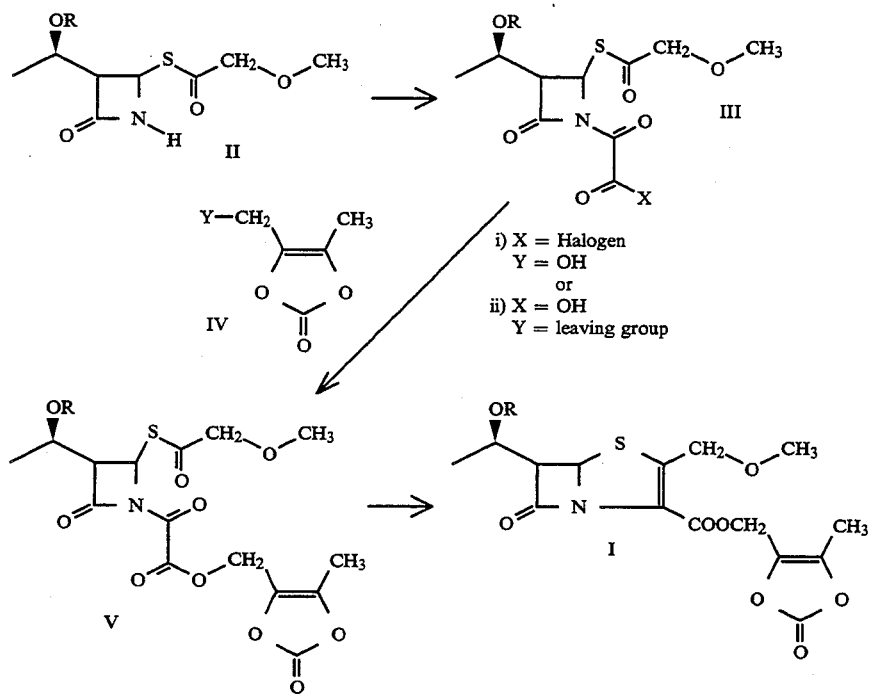

Azetidinoes II are reacted in an inert solvent with oxalyl halides, especially oxalyl chloride or oxalyl bromide in the presence of an inorganic or organic base or an acid scavenger affording halooxalyl azetidinones of formula III. Reaction of azetidinones II with oxalyl halides is performed in an aprotic solvent at a temperature ranging from −70° C. to +40°, preferably between −40° C. and room temperature. Preferred organic solvents are dichloromethane, chloroform, benzene, toluene, xylenes (as single isomer or a mixture thereof), carbon tetrachloride, ethyl acetate, propyl acetate, butyl acetate, tetrahydrofuran, dioxane, acetonitrile, diisopropylether, methylethylketone.

Said reaction is usually performed in the presence of a tertiary organic base either aliphatic or aromatic or alicyclic such as triethylamine, trimethylamine, diisopropyl ethylamine, aniline, pyridine, lutidine, collidine, quinoline, N-methyl morpholine, N-methyl pyrrolidine, N-methylpiperidine, diazobicyclooctane (DABCO).

Inorganic base are also effective, preferred ones are alkaline bicarbonates or carbonates such as sodium bicarbonate, calcium carbonate, cesium carbonate, magnesium carbonate, potassium carbonate.

Amongst acid scavengers molecular sieves are the preferred ones. Mixtures of acid scavengers, inorganic bases and organic bases may be conveniently employed.

For alternative processes (i) and (ii):

(i) Crude solutions or mixtures of halooxalyl azetidinones III are treated with 4-hydroxymethyl-5-methyl-1,3 -dioxolen-2-one (formula IV wherein Y is hydroxy group), in the presence of an acid scavenger or an organic or inorganic base, to give the compounds of the formula V. This method of obtaining compound V is the preferred one.

Preferred organic or inorganic bases or acid scavengers are as described above. Preferred range of temperature is $-30°$ to room temperature.

(ii) Alternatively conversion of compounds of formula III into derivatives of formula V can be carried out by treating the acids of formula III in which X represents hydroxy group, with compounds of formula IV wherein Y is a leaving group, especially a halide or an alkyl or arylsulphonyloxy group in the presence of organic or inorganic bases.

The conversion from compounds III in which X is halogen atom to those in which X is hydroxy group is usually performed by simply mixing the crude solution of III with water or by treatment with dilute aqueous basic or acid solutions. Following drying over a dehydrating agent such as alkaline sulphate or by azetropic removal of water the compounds of the formula III wherein X is a hydroxy group thus obtained, may be directly treated with alkylating agents IV in which Y is a leaving group or the solvent may be removed and substituted by another aprotic solvent.

Suitable organic solvents for the conversion of X in the formula III from halogen to hydroxy group are polar aprotic solvents such as acetonitrile, dimethylformamide, propionitrile, dimethylsulphoxide, hexamethylphosphoramide, sulpholane and acetone. Preferential reaction temperature ranges from $-20°$ to $+60°$ C., preferred organic or inorganic bases or acid scavengers are as described above. Addition of alkaline halides such as sodium iodide is often beneficial to accelerating the esterification process.

Preferred leaving groups Y (for derivatives IV) are chloro, bromo or iodo or a mesyloxy, tosyloxy or triflyloxy group.

The resultant compound V is not generally isolated. In most cases, when not mixable with water, solutions of V are simply washed with water or aqueous solutions (brine, dilute aqueous hydrochloric acid, dilute aqueous sodium bicarbonate, etc.) to remove inorganic or ammonium halides and, if present, excess of 4-hydroxymethyl-5-methyl-1,3-dioxolen-2-one of formula IV. If mixable with water, solutions of V are concentrated in vacuo then diluted with toluene or xylene and ashed with aqueous solutions.

The compound of formula V is typically cyclised in the presence of a trialkylphosphite such as a tri($C_1$-$C_4$ alkyl) phosphite. Prior to treatment with a trialkylphosphite, solutions of V are generally dried over a dehydrating agent such as sodium sulphate, magnesium sulphate or calcium sulphate or by azeotropic removal.

Eventually solutions of V, following additions of trialkylphosphites, preferably trimethylphosphite or triethylphosphite, are heated at a temperature ranging from $+60°$ to $+150°$ C., providing penems I which are isolated by crystallization or silica gel chromatography in high overall yield.

The optional final removal of the protecting group R may be carried out by known methods, such as, for instance hydrogenolysis, e.g. in the presence of palladium on charcoal as catalysts or by hydrolysis, either acid hydrolysis, e.g. with acetic acid or oxalic acid, or neutral hydrolysis in the presence of $SiO_2$, or basic hydrolysis, or hydrolysis under reductive conditions, for example by the use of Fe/$NH_4Cl$, Zn/$H^+$ or of $Na_2S_2O_4$, or by desilylation with fluoride salts, such as KF or (But)$_4$NF.$3H_2O$.

All the above cited reactions are preferably carried out in an inert atmosphere e.g. under nitrogen or argon and in the absence of moisture. The resulting penem of formula I, useful as an antibacterial agent, may be formulated as a pharmaceutical composition. The pharmaceutical composition also comprises a pharmaceutically acceptable carrier or diluent.

As said above, the present invention relates also to the preparation of compound of the formula IV in which Y is a hydroxy group by treatment of the compound of the formula IV in which Y is a halogen atom with silver nitrate and subsequent reduction under dissolving metal conditions. A preferred reducing agent is zinc powder in a mixture of acetic acid and an inert organic solvent.

The compound of formula IV in which Y is a hydroxy group may be also obtained as described in JP-A-59-212488 (1984). The starting compounds of the formula IV in which Y is a halogen atom or a leaving group are described in Chem. Pharm. Bull 32, 2241 (1984), 36 394 (1988) and Chemical Abstracts 101:110894f.

The following Examples illustrate the invention without limiting it.

EXAMPLE 1

(5-methyl-2-oxo-1,3-dioxolen-4-yl)methyl(5R,6S)-6-[(1R)tert-butyldimethylsilyloxyethyl]-2-methoxymethylpenem-3-carboxylate.

Method A

To a stirred solution of (3S,4R)-3-[(1R)tert-butyl dimethylsilyloxyethyl]-4-(methoxyacetyl)thioazetidin-2-one (8.2 g) in dry toluene (150 ml) at 5° C. under nitrogen, oxalyl chloride (2.1 ml) was added, soon followed by the dropwise addition of triethylamine(6.6 ml) in toluene (30 ml). After 20 minutes a solution of 4-hydroxymethyl-5-methyl-1,3-dioxolen-2-one (6 g) in methylene chloride (20 ml) was added and the resulting mixture was stirred 20 minutes at 30° C.

The organic solution was washed with water (250 ml) then dried over sodium sulphate, and concentrated to ⅓ of the initial volume.

Triethylphosphite (7 ml) in xylene (80 ml) was added and the solution was heated at reflux for 2 hours. Cyclohexane (100 ml) was added to the cooled reaction mixture. After washing with water (2×300 ml), the organic phase was concentrated and chromatographed over silica gel (eluting with cyclohexane-ethyl acetate mixtures) affording the title product as an oil (6.7 g).

Method B

To a stirred solution of (3S,4R)-3-[(1R)tert-butyldimethyl silyloxyethyl]-4-(methoxyacetyl)thioazetidin-2one (8.2 g) in dry methylene chloride (100 ml), calcium carbonate (2 g) and oxalyl chloride (4 ml) were added sequentially while keeping the temperature under 0° C.

N,N-diisopropylethylamine (6 ml) in CH$_2$Cl$_2$ (10 ml) was added dropwise at 0° C. and the resulting yellow mixture was stirred for 30 minutes.

After addition of water (200 ml) stirring was continued for 10 minutes. The organic phase was dried over sodium sulphate and evaporated. The residue (11.2 g) was dissolved in acetonitrile (80 ml), thence treated with 4-bromomethyl-5-methyl-1,3-dioxolen-2-one (6.6 g) and triethylamine (3.8 g).

The reaction mixture was stirred at room temperature for 1 h at 45° C.

After removal of the solvent, water and ethyl acetate (1:1) were added. The organic phase was dried and concentrated under vacuum giving a light colored oil (15.2 g). Triethyl phosphite (13 ml) in xylene (60 ml) was added and the resulting solution was heated at reflux for 1 h.

Following addition of cyclohexane (200 ml) and washing with water (2×200 ml) the organic phase was dried (Na$_2$SO$_4$) and concentrated. Flash chromatography of the residue (cyclohexane ethyl acetate mixture as eluent), afforded the title product as an oil (5.3 gl.

NMR (90 MHz, CDCl$_3$) 0.09 (6H, s) 0.87 (9H, s) 1.23 (3H,d, J=6.5 Hz) 2.18 (3H,s) 3.41 (3H,s) 3.68 (1H,dd, J=1.5 and 4.5 Hz) 4.20 (1H,m) 4.62 (2H, ABq, J=15.5 Hz) 4.93 (1H, ABq, J=13.5 Hz) 5.58 (1H, d, J=1.5 Hz)

EXAMPLE 2

(5-methyl-1,3-dioxolen-2-on-4-yl)methyl (5R,6S)-6-[(1R) hydroxyethyl]-2-methoxymethylpenem-3carboxylate.

A solution of (5-methyl-2-oxo-1,3-dioxolen-4-yl)methyl (5R,6S)-[(1R)tert-butyldimethylsilyloxyethyl]-2-methoxymethylpenem-3-carboxylate (6g) in tetrahydrofuran (30 ml) was treated with acetic acid (1 ml) and tetrabutylammonium fluoride trihydrate (3 g) and left to stand at room temperature (r.t.) for 40 h. The reaction mixture was poured into water-ethyl acetate.

The organic phase was dried, concentrated and chromatographed (SiO$_2$, cyclohexane-ethyl acetate mixtures as eluent) to afford the title product as white powder (3.5 g)

[α]$_D$= +139° 1% MeOH, 23° C.)

EXAMPLE 3

4-hydroxymethyl-5-methyl-1,3-dioxolen-2-one

A solution of 4-bromomethyl-5-methyl-1,3-dioxolen-2-one (960 mg) in dry CH$_3$CN (15 ml) was treated with silver nitrate (830 mg). The mixture was stirred 15 minutes at r.t. diluted with benzene (20 ml) and filtered.

The filtrate was heated at reflux for 2.5 h, then cooled to 20° C. and treated with acetic acid (10 ml) and excess zinc powder.

Stirring was continued for few hours at r.t. (until completion of the reaction: TLC monitoring: ethyl acetate-cyclohexane 1:1, detection with aqueous KMnO$_4$).

Removal of the solvent in vacuo and flash chromatography of the residue afforded a light yellow oil (470 mg).

Alternatively the mixture was filtered, concentrated, and the residue purified by distillation under reduced pressure (108° C./0.5 mmHg)

IR (CHCl$_3$)ν$_{max}$ 3300–3600, 1810 (strong), 1740 cm$^{-1}$ NMR (CDCl$_3$, 90 MHZ)δ: 2.13 (3H, s) 2.6 (1H, br.s, exch.D$_2$O) 4.30 (2H, S)

We claim:

1. A process for the preparation of a compound of formula (I):

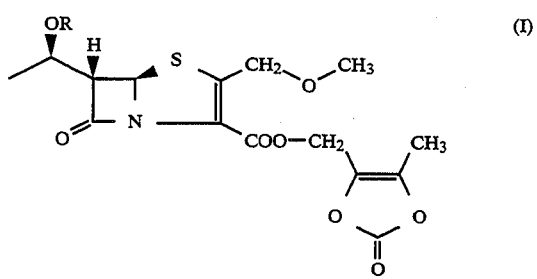

wherein R represents a hydrogen atom or a hydroxy protecting group, comprising reacting a compound of formula (II):

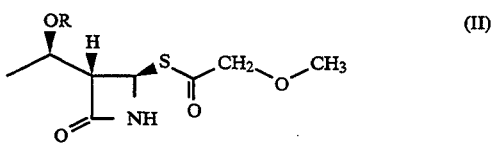

wherein R is as defined above, with an oxalyl halide in an inert solvent in the presence of an inorganic or organic base or an acid scavenger to produce a compound of the formula (III):

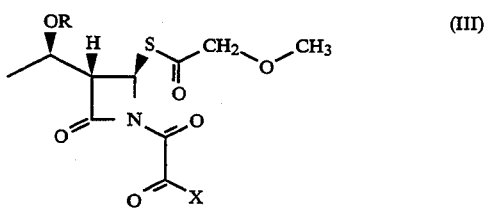

wherein R is as defined above and X is a halogen atom, treating said compound of the formula (III) with a compound of the formula (IV):

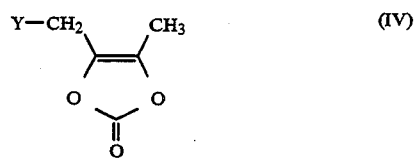

wherein Y is a hydroxy group in the presence of molecular sieves or an organic or inorganic base to produce a compound of the formula (V):

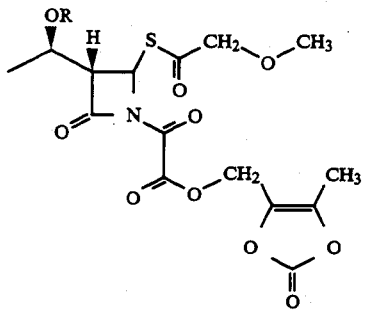

wherein R is as defined above, and
cyclizing said compound of the formula (V) in the presence of a trialkylphosphite.

2. A process according to claim 1 in which the oxalyl halide is oxalyl chloride or oxoalyl bromide.

3. The process of claim 2, wherein R is a hydroxy protecting group, further comprising the step of removing said hydroxy protecting group in said compound of formula (I) to obtain the compound of formula (I) wherein R is a hydrogen atom.

4. The method of claim 3, wherein said hydroxy protecting group is selected from the group consisting of:
a) a silyl group —SiR$^1$R$^2$R$^3$, wherein R$^1$, R$^2$, R$^3$ are each independently C$_1$–C$_6$ alkyl, aryl, C$_1$–C$_6$ alkoxy, aryloxy or a halogen atom;
b) a

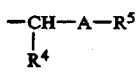

group, wherein R$^4$ is hydrogen, C$_1$–C$_6$ alkyl or aryl, A is oxygen or sulfur, R$^5$ is a C$_1$–C$_6$ alkyl, aryl or heterocyclyl group, or R$^4$ and R$^5$ taken together form a part of a C$_5$–C$_6$ ring;
c) a

group wherein R$^6$ is an alkyl, alkenyl, aryl, heterocyclyl or heterocyclylmethyl group; and
d) a

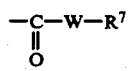

wherein R$^7$ is hydrogen or as defined above under R$^6$ and W is a bond, a carbonyl

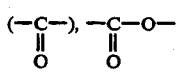

or a

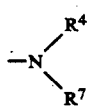

group, wherein R$^4$ and R$^7$ are as defined above.

5. The process of claim 4, wherein said hydroxy protecting group is selected from the group consisting of trimethylsilyl, triethylsilyl, tert-butyldimethylsilyl, t-hexyldimethylsilyl, tert-butoxydiphenylsilyl, methoxymethyl, methylthiomethyl, benzyloxymethyl, tert-butoxymethyl, tetrahydropyranyl, tetrahydrothiopyranyl, tetrahydrofuranyl, 4-methoxytetrahydropyranyl, 1-ethoxyethyl, 1-phenoxyethyl, allyloxycarbonyl, benzyloxycarbonyl, trimethyl silylethoxycarbonyl, p-nitrobenzyloxycarbonyl, methoxybenzyloxycarbonyl, o-nitrobenzyloxycarbonyl, 3,4-dimethoxybenzyloxycarbonyl, phenoxycarbonyl, vinyloxycarbonyl, trichloroethoxycarbonyl, formyl, acetyl, propionyl, butyryl, C$_5$–C$_{14}$ alkanoyl, benzoyl, phenylacetyl, phenoxyacetyl, chloroacetyl, dichloroacetyl, trichloroacetyl, trifluoroacetyl, methoxyacetyl, pivaloyl, crotonyl, acrylyl, glyoxylyl, methoxyoxalyl, allyloxyoxalyl, (5-methyl-2-oxo-1,3-dioxolen-4-methoxyoxalyl, butoxyoxalyl, phenoxyoxalyl, oxamyl and carbamoyl.

6. The process of claim 1, wherein said reacting step and said treating step are conducted in a single pot.

7. The process of claim 1, wherein said reacting step is performed at a temperature of from −70° C. to 40° C.

8. The process of claim 11, wherein said organic solvent is selected from the group consisting of dichloromethane, chloroform, benzene, toluene, xylenes (as a single isomer or a mixture thereof), carbon tetrachloride, ethyl acetate, propyl acetate, butyl acetate, tetrahydrofuran, dioxane, acetonitrile, diisopropylether and methylethylketone.

9. The process of claim 11, wherein said reacting step is performed in the presence of a tertiary organic base selected from the group consisting of triethylamine, trimethylamine, diisopropyl ethylamine, aniline, pyridine, lutidine, collidine, quinoline, N-methyl morpholine, N-methyl pyrrolidine, N-methylpiperidine and diazobicyclooctane.

10. The process of claim 11, wherein said reacting step is performed in the presence of an inorganic base selected from the group consisting of sodium bicarbonate, calcium carbonate, cesium carbonate, magnesium carbonate and potassium carbonate.

11. The process of claim 7, wherein the acid scavenger of said reacting step is molecular sieves.

12. The process of claim 1, wherein said treating step is performed in the presence of an organic base selected from the group consisting of triethylamine, trimethylamine, diisopropyl ethylamine, aniline, pyridine, lutidine, collidine, quinoline, N-methyl morpholine, N-methyl pyrrolidine, N-methylpiperidine and diazobicyclooctane or an inorganic base selected from the group consisting of sodium bicarbonate, calcium carbonate, cesium carbonate, magnesium carbonate and potassium carbonate.

13. The process of claim 12, wherein said treating step is performed at a temperature of from −30° C. to room temperature.

14. The process of claim 8, wherein said reacting step, said treating step and said cyclizing step are performed in a single pot.

15. The process of claim 14, wherein said trialkylphosphite is a tri(C$_1$–C$_4$ alkyl)phosphite.

16. The process of claim 15, wherein said cyclizing step is performed at a temperature of from 60° to 150° C.

17. The process of claim 3, wherein said removing of said protecting group is performed by a method selected from the group consisting of:
(A) hydrogenolysis in the presence of palladium on charcoal;

(B) acid hydrolysis with acetic acid or oxalic acid;
(C) neutral hydrolysis in the presence of SiO$_2$;
(D) basic hydrolysis;
(E) hydrolysis under reductive conditions using a combination of Fe and NH$_4$Cl, a combination of Zn and H$^+$, or Na$_2$S$_2$O$_4$; and
(F) desilylation with KF or (But)$_4$NF trihydrate.

18. The method of claim 17, wherein said hydroxy protecting group is selected from the group consisting of trimethylsilyl, triethylsilyl, tert-butyldimethylsilyl, t-hexyldimethylsilyl and tert-butoxydiphenylsilyl, and said removing is performed by desilylation with KF or (But)$_4$NF trihydrate.

19. (5-Methyl-2-oxo-1,3-dioxolen-4-yl)methyl (5R,6S)-6-[(lR)-tert-butyldimethylsilyloxyethyl]-2-methoxymethylpenem-3-carboxylate.

* * * * *

UNITED STATES PATENT AND TRADEMARK OFFICE
CERTIFICATE OF CORRECTION

PATENT NO. : 5,416,208

DATED : MAY 16, 1995

INVENTOR(S): ETTORE PERRONE ET AL

It is certified that an error appears in the above-identified patent and that said Letters Patent is hereby corrected as shown below:

On the Title page, Column 1, delete item [63] in its entirety, and replace with

--[63] Continuation of Ser. No. 77,967, Jun. 18, 1993, abandoned, which is a continuation of Ser. No. 655,458, Mar. 5, 1991, abandoned, which is the national stage of PCT/EP90/01060, filed July 3, 1990.--.

Signed and Sealed this

Twelfth Day of September, 2000

*Attest:*

Q. TODD DICKINSON

*Attesting Officer*       *Director of Patents and Trademarks*